US00PP21697P3

(12) United States Plant Patent
Leis et al.

(10) Patent No.: US PP21,697 P3
(45) Date of Patent: Feb. 8, 2011

(54) APPLE TREE NAMED 'CIVNIRED S'

(50) Latin Name: *Malus domestica*
Varietal Denomination: Civnired S

(75) Inventors: Michelangelo Leis, Ferrara (IT); Alessio Martinelli, Gaibanella (IT); Silvia Salvi, Ferrara (IT); Francesco Tagliani, Argenta (IT)

(73) Assignee: C.I.V. Consorzio Italiano Vivaisti - Societa Consortile A R.L., Ferrara (IT)

( * ) Notice: Subject to any disclaimer, the term of this patent is extended or adjusted under 35 U.S.C. 154(b) by 0 days.

(21) Appl. No.: 12/587,073

(22) Filed: Sep. 30, 2009

(65) Prior Publication Data

US 2010/0263099 P1 Oct. 14, 2010

(30) Foreign Application Priority Data

Apr. 14, 2009 (QZ) ..... 2009/0687

(51) Int. Cl.
*A01H 5/00* (2006.01)

(52) U.S. Cl. ..... Plt./161

(58) Field of Classification Search ..... Plt./161
See application file for complete search history.

*Primary Examiner*—Susan B McCormick Ewoldt
(74) *Attorney, Agent, or Firm*—Foley & Lardner LLP

(57) ABSTRACT

A new and distinct *Malus domestica Borkh.* variety of apple tree named 'CIVNIRED S', particularly characterized by deep bright red, striped skin color of mature fruit; more intense and extension overcolor of mature fruit; outstanding eating quality (taste and crispness) of mature fruit; and excellent shelf life of mature fruit.

3 Drawing Sheets

Latin name of the genus and species of the plant claimd: *Malus domestica.*

Variety denomination: 'CIVNIRED S'.

PRIORITY CLAIM

This application claims priority under 35 U.S.C. §119(f) of the European Union-Community Plant Variety Rights No. 2009/0687 filed Apr. 14, 2009.

STATEMENT REGARDING SPONSORED RESEARCH OR DEVELOPMENT

None.

BACKGROUND OF THE INVENTION

The present invention relates to a new and distinct variety of apple tree, botanically known as *Malus domestica Borkh.* of the *Rosaceae* family, and hereinafter referred to by the 'CIVNIRED S'.

The new *Malus* variety 'CIVNIRED S' was discovered by the inventors, Michelangelo Leis, Silvia Salvi, Francesco Tagliani and Alessio Martinelli, in August of 1999 in a block of *Malus domestica* Borkh. apple trees designated 'CIVNI' (patented, U.S. Plant Pat. No. 14,177) growing in a cultivated area of an apple farm located in Laces (South Tyrol), Italy. The new *Malus* variety 'CIVNIRED S' originated as a sport mutation of a limb of one of the 'CIVNI' apple trees growing in the apple farm located in Laces (South Tyrol), Italy. The new *Malus* 'CIVNIRED S' was selected by the inventors based on the distinctive fruit characteristics of 'CIVNIRED S'. In particular, the mature fruit of 'CIVNIRED S' has a more intense and greater extension of the bright red overcolor than 'CIVNI', while the outstanding eating quality (taste and crispness) and excellent shelf life of the mature fruit remains unchanged from 'CIVNI'.

The new *Malus* 'CIVNIRED S' was first selected for propagation and further testing by the inventors in 1999 in a controlled environment in S. Giuseppe di Comacchio (Ferrara), Italy. Asexual reproduction of the new *Malus* 'CIVNIRED S' by grafting and budding onto M9 rootstock (unpatented) was first performed in March of 2001 in an apple farm located in S. Giuseppe di Comacchio (Ferrara), Italy, and it has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'CIVNIRED S' which in combination distinguish this apple tree as a new and distinct variety:

1. deep bright red, striped skin color of mature fruit;
2. more intense and extension overcolor of mature fruit;
3. outstanding eating quality (taste and crispness) of mature fruit; and
4. excellent shelf life of mature fruit.

In comparison to the parental variety, *Malus* 'CIVNI' (patented, U.S. Plant Pat. No. 14,177), the new *Malus* 'CIVNIRED S' differs by the following traits described in Table 1:

TABLE 1

| Characteristic | New Variety 'CIVNIRED S' | Parental & Comparison Variety 'CIVNI' (U.S. PP14,177) |
|---|---|---|
| Hue of over color of mature fruit | Deep bright red RHS 44A | Orange red RHS 33A to RHS 34A |
| Relative area of overcolor | Greater than 'CIVNI' 85% to 100% | Less than 'CIVNIRED S' 60% to 100% |

Of the many commercial varieties known to the present inventors, the most similar in comparison to the new *Malus*

'CIVNIRED S' is the parental variety 'CIVNI' (patented, U.S. Plant Pat. No. 14,177), as compared in Table 1 above.

BRIEF DESCRIPTION OF THE PHOTOGRAPHS

The accompanying photographs illustrate the overall appearance of the new *Malus* 'CIVNIRED S' showing the colors as true as is reasonably possible with colored reproductions of this type. Colors in the photographs may differ slightly from the color values cited in the detailed botanical description, which accurately describe the color of 'CIVNIRED S'.

DETAILED BOTANICAL DESCRIPTION

Figure 1:
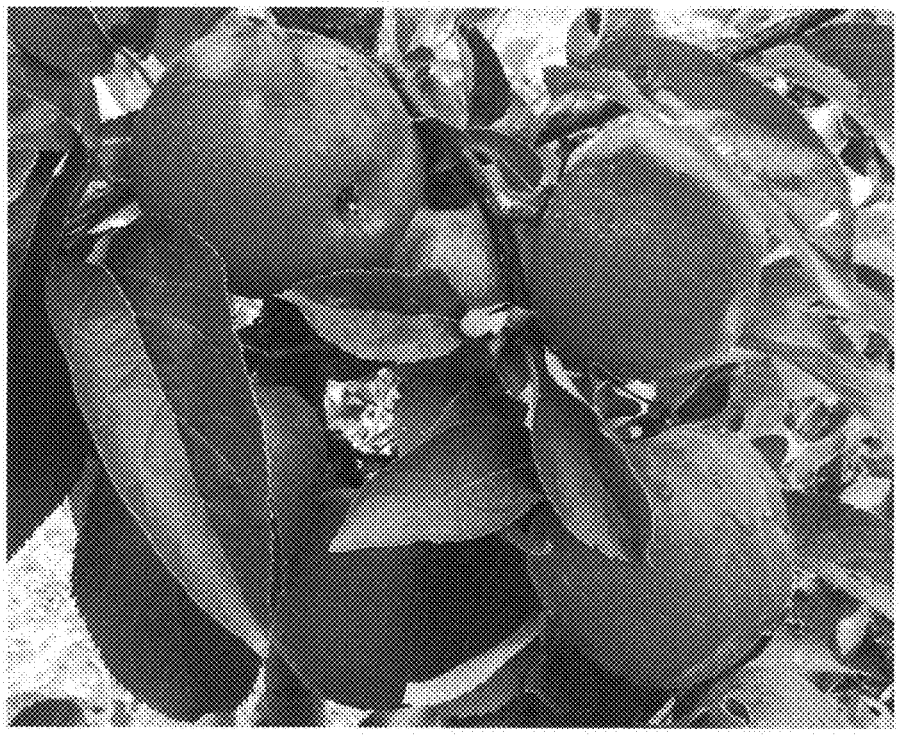
FIG. 1 shows a perspective view of typical apples of 'CIVNIRED S' originating as a sport limb mutation of a 'CIVNI' tree (top) compared to typical apples of 'CIVNI' on a non-mutated branch of the same 'CIVNI' tree.
Figure 1:
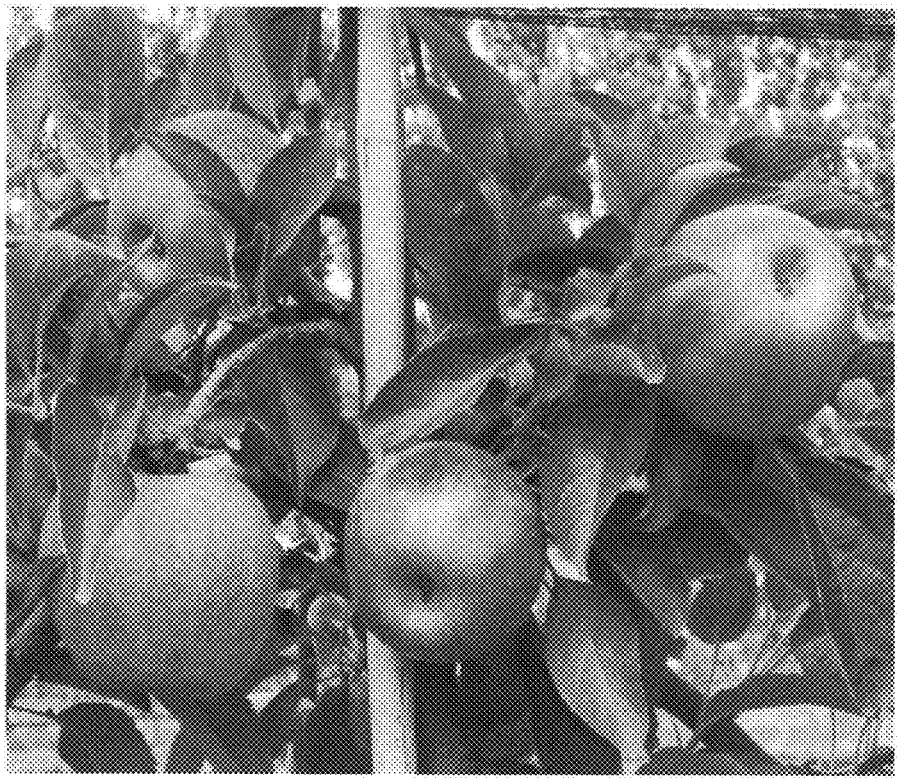
Figure 2:
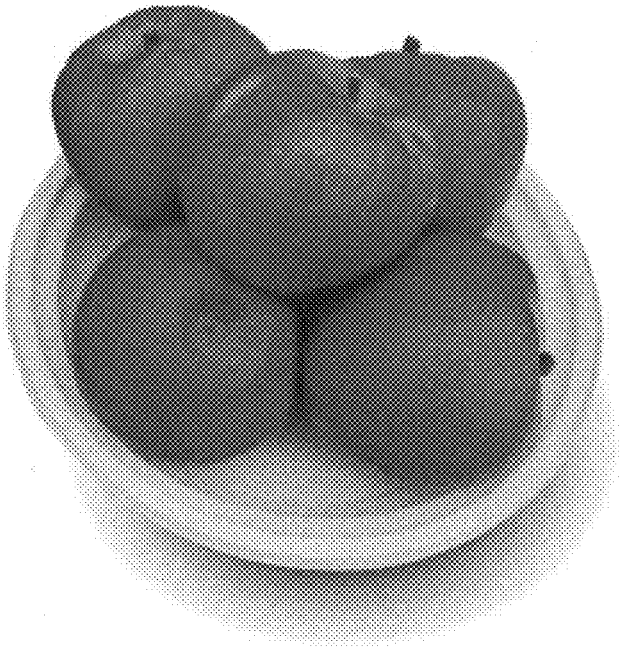
FIG. 2 shows a perspective view of typical mature apples of 'CIVNIRED S' (top) compared to typical mature apples of 'CIVNI' (bottom).
Figure 2:
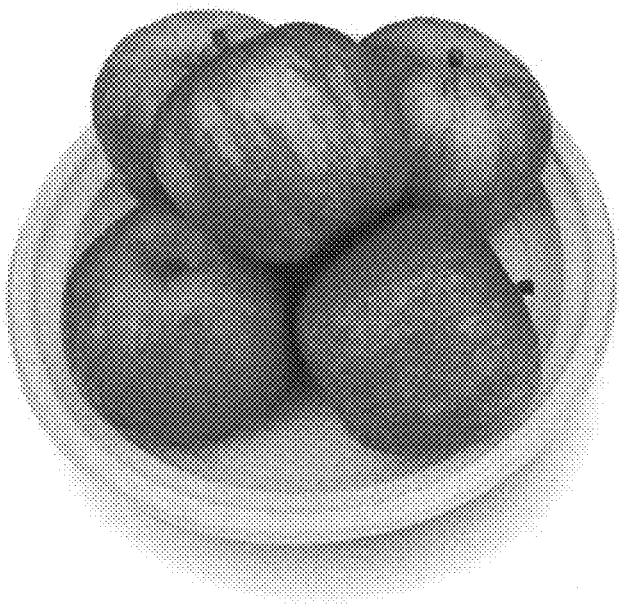
Figure 3:
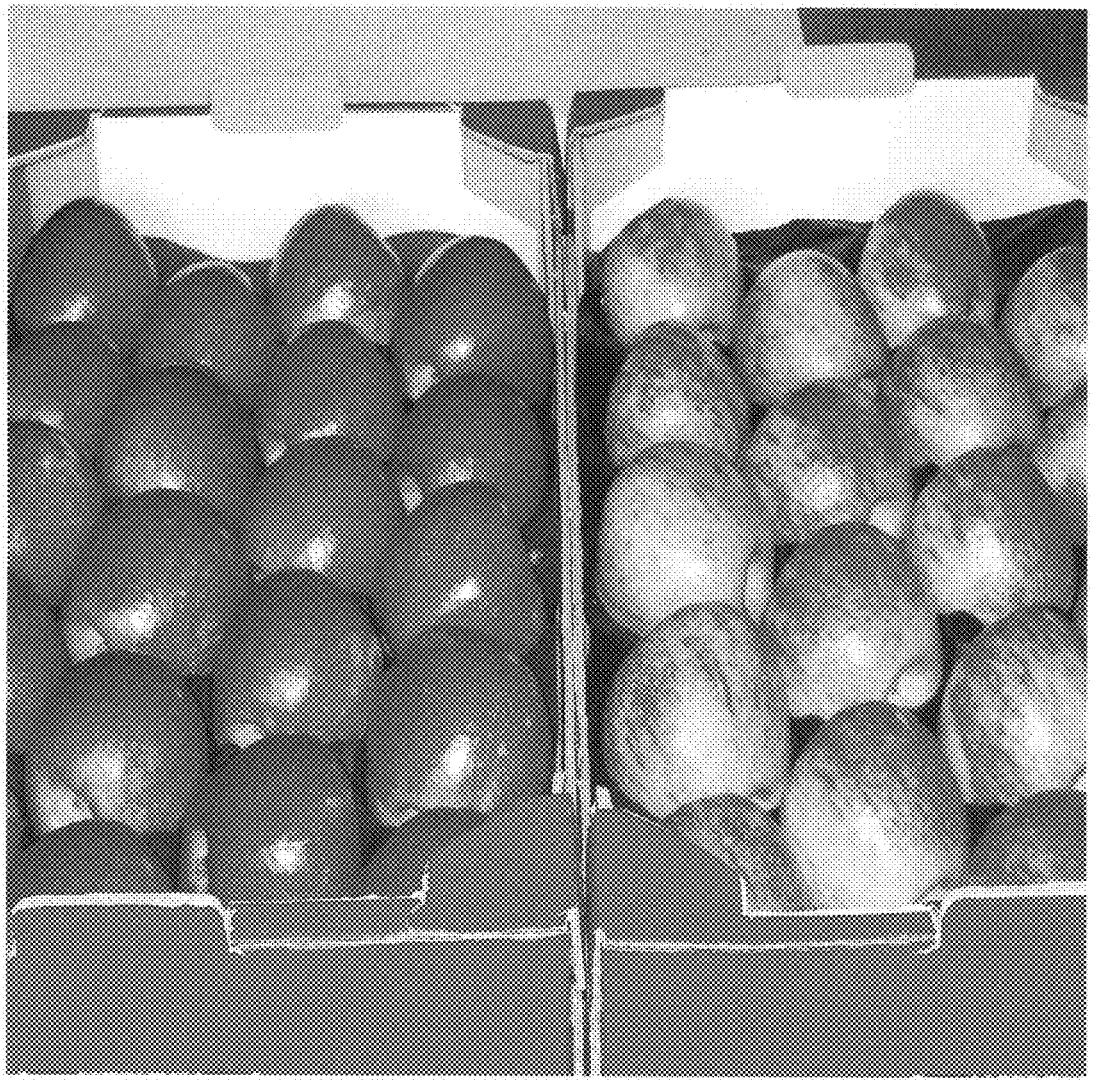
FIG. 3 shows a perspective view of box of typical mature apples 'CIVNIRED S' (on the left) compared to typical apples of 'CIVNI' (on the right).

The new *Malus* 'CIVNIRED S' has not been observed under all possible environmental conditions. The phenotype of the new variety may vary with variations in environment such as temperature, light intensity, and day length without any change in the genotype of the apple tree.

The aforementioned photographs, together with the following observations, measurements and values describe trees of 'CIVNIRED S' as grown in the apple farm in S. Giuseppe di Comacchio (Ferrara), Italy, near the Adriatic sea, at zero (0) meters above sea level, and which are grown under conditions which closely approximate those generally used in commercial practice. The climate of the apple farm where 'CIVNIRED S' is grown is temperate continental (about 44° 45 North, 12° 11 East) with high summer temperatures (maximum summer temperature of about 40° C.) and low winter temperatures (minimum winter temperature of about −12° C.). The soil of the apple farm where 'CIVNIRED S' is grown is sandy, and the soil is treated with manure every year, the trees are irrigated with a drip irrigation system. 'CIVNIRED S' trees are grafted on M9 rootstock (unpatented) are planted at a distance of about 1 meter between trees and 3.5 meter between rows, which is the typical orchard planting distance. The training system is by central leader.

Unless otherwise stated, the detailed botanical description includes observations, measurements and values based on five (5) year old 'CIVNIRED S' trees that were grown in the apple farm in S. Giuseppe di Comacchio (Ferrara), Italy, from 2004 years to 2008. Quantified measurements are expressed as an average of measurements taken from a number of trees of 'CIVNIRED S'. The measurements of any individual tree, or any group of trees, of the new variety may vary from the stated average.

Color references are made to The Royal Horticultural Society Colour Chart (R.H.S.), 2001 Edition, except where general colors of ordinary significance are used. Color values were taken under daylight conditions at approximately 3:00 p.m. in the apple farm in S. Giuseppe di Comacchio (Ferrara), Italy.

All of the trees of 'CIVNIRED S', insofar as they have been observed, have been identical in all the characteristics described below.

Classification:

*Botanical.*—*Malus domestica Borkh.*

Parentage: Limb sport mutation of *Malus domestica Borkh.* 'CIVNI' (patented, U.S. Plant Pat. No. 14,177).

Propagation:

*Type.*—Budding and grafting on M9 rootstock (unpatented).

*Locality where grown and observed.*—S. Giuseppe di Comacchio (Ferrara), Italy.

Growing conditions:

*Light intensities.*—Full sunlight or slight shade.

*Pruning or trimming requirements.*—Similar to 'GALA' variety with weaker vegetation. Requires regular renewal of fruiting branches and shoots. Does well as a slender spindle. High flower numbers, preferably reduced by regular pruning and fruit thinning.

Tree:

*Age.*—Observed trees were five (5) years old.

*Vigor.*—Moderate vigor.

*Form.*—Upright, good ramification.

*Branching habit.*—Main branches angle about 50° with respect to trunk if allowed to grow naturally.

*Density.*—Medium density; about 2,800 trees per hectare.

*Type of bearing.*—Early beginning of production; good productivity; regular and abundant flowering; full blooming each year (no alternate bearing). Predominance of bearing on spur.

*Production on five* (5) *years old tree.*—About 18 kg per tree.

*Average size at maturity* (*on five* (5) *years old tree*).—Height: About 2.80 m. Spread: About 1.20 m.

*Trunk caliper* (*at* 10 *cm above point of grafting*).—About 5.5 cm.

*Trunk texture.*—Smooth with numerous lenticels.

*Trunk bark color.*—Greyed-green, RHS 197A.

*Trunk lenticels.*—Length: About 3.5 mm. Width: About 1.5 mm. Color: Grey-brown, RHS 199B. Density: 2.45 per $cm^2$.

*Branches.*—Number per tree: About 22. Angle: At emergence, angles range from 50° to 80°. Length (at five (5) years): Maximum of 90 cm; minimum of 70 cm. Diameter (at five (5) years): About 15 mm to 12 mm. Texture: Smooth. Color: Mature (after about five (5) years): Greyed-green, RHS 197 A New Growth: Brown, RHS 200 D. Internode length: About 5.6 cm to 2.3 cm. Internode diameter: About 14 mm to 12 mm. Branch lenticels: Length: About 1.2 mm. Width: About 0.7 mm. Color: Greyed-orange, RHS 165B. Density: About 3.43 per $cm^2$.

*Spur.*—Present: Yes. Distance between each spur: On three (3) year old branches, the distance is about 25 mm to 45 mm. Number of fruit per spur: About 2 to 4.

Foliage:

*Arrangement.*—Alternate, simple, petiolated.

*Lamina.*—Average size (from observation of four (4) fully expanded leaves in June, 2008 *in S. Giuseppe di Comacchio* (Ferrara), Italy: Length: About 96.3 mm (range from 89 mm to 101 mm). Width: About 52.2 mm (range from 45 mm to 59 mm). Length/width ratio: 1.84. Overall shape: Elliptical-elongated and slightly undulated. Base shape: Acute. Apex shape: Acute. Margin: Biserrate. Texture: Upper surface: Glossy. Under surface: Slightly pubescent. Attitude in relation to shoot: Outwards. Color (mature leaves):

Upper surface: Green, RHS 137A. Under surface: Yellow-green, RHS 148B. Venation: Type: Prominent, pinnate venation, from central vein to the leaf edge Color: Yellow-green, RHS 145C.

*Petiole.*—Length: About 31 mm. Diameter: About 1.83 mm. Texture: Slightly pubescent. Color: Greyed-green, RHS 191B.

*Stipule.*—Arrangement: Opposite. Length: About 5 mm to 16 mm. Width: About 0.5 mm to 2.0 mm.

*Distance of stipules from basal attachment of petiole.*—About 0.5 mm to 5 mm.

Inflorescence:

*Blooming time (in S. Giuseppe di Comacchio (Ferrara), Italy).*—Mid-season. First bloom: On or about April 8$^{th}$. Full bloom: On about April 12$^{th}$.

*Blooming period.*—About 11 to 13 days.

*Fragrance.*—Light, similar to other apple varieties.

*Number of flowers per inflorescence.*—About 5 to 6.

*Buds.*—Number per spur: About One (1). Shape: Pointed. Length: About 8.2 mm. Width: About 4.1 mm. Texture: Slightly pubescent. Color: Brown, RHS 200C.

*Petals.*—Number per flower: Five. Size: Length: About 16.97 mm. Width: About 12.60 mm. Length/width ratio: 1.35. Overall shape: Elliptic-ovate. Apex shape: Obtuse. Base shape: Obtuse. Texture (upper and under surfaces): Smooth. Margin: Entire. Color (when fully opened): Upper surface: White, RHS 155D, with traces of red-purple, RHS 69B. Under surface: White, RHS 155D, with traces of red-purple, RHS 70B. Color (unopened): Red purple, RHS 70B.

*Sepals.*—Number per flower: Five. Size: Length: About 7.08 mm. Width: About 3.04 mm. Overall shape: Pointed acute, recurved downward, gamosepalous. Apex shape: Acute. Base shape: Fused. Texture (upper and under surfaces): Hairy. Margin: Entire. Color: Upper and under surfaces: Green, RHS 139C.

Fruit:

*Keeping quality.*—The fruit keeps very well on the tree. It can be stored in cold (+2° C.) temperature conditions for up to five (5) months without losing firmness and juiciness. It has a shelf life up to 2 weeks without losing firmness and juiciness.

*Maturity when described.*—Mid August in S. Giuseppe di Comacchio (Ferrara), Italy.

*Maturity period after full bloom.*—About 125 days after full bloom on April 12$^{th}$.

*Date of first and last picking (harvest).*—About August 15$^{st}$ to August 20$^{th}$ in S. Giuseppe di Comacchio (Ferrara), Italy.

*Type.*—Pome.

*General shape.*—Conical-truncated, slightly asymmetric, with non-prominent lobes at calyx ends.

*Average weight.*—About 235 g.

*Fruit size.*—Average height: About 74 mm. Average diameter (at widest point): About 82 mm. Position of maximum diameter: At about ½ of height near stem end.

*Stem.*—Length: About 20 mm to 25 mm. Diameter: About 3.7 mm. Color: Greyed-orange, RHS 172B.

*Stem cavity.*—Slight russet around cavity. Depth: About 15.8 mm. Width: About 21.5 mm.

*Basin cavity.*—Depth: About 13.1 mm. Width: About 33.0 mm. Position of sepals: Erect, convergent and free.

*Skin.*—Appearance: Medium thickness; smooth texture; dry and slightly waxy when overripe. No evidence of cracking tendency observed with apple maturity. Thickness: Medium. Texture: Smooth. Bloom: Absent. Greasiness: Slightly waxy when overripe. Firmness (at picking time): 7.5 to 9.0 kg/cm$^2$. Overall color: Red, RHS 44A. Ground color: Yellow-green, RHS 151B. Over color: Red, RHS 44A to RHS 44B (85% to 100%). Color markings: Solid flush with strongly defined stripes. Skin lenticels: Length: About 0.45 mm. Width: About 0.39 mm. Color: Greyed-orange, RHS 164D. Density: About 7.2 per cm$^2$.

*Flesh.*—Color: Yellow, RHS 11D. Texture: Firm and juicy, of medium texture. Aroma: High level of aroma. Flavor: Sweet flavor, with sweet aftertaste. Eating quality: Excellent, with good sugar-acid balance. Firmness (at picking time): About 7.5 kg to 9.0 kg. Soluble solids (at picking time): About 14% to 15%. Sugar content (at picking time): 13.8 to 14.8 Brix. Acidity/starch (at picking time): 9 to 7.5 g/lt starch at 2.0-2.5 on a scale 1 to 5.

*Core.*—Symmetry of core: Symmetric with defined bundles. Distinctness of core lines: Strong. Length: About 26 mm. Width: About 36 mm.

*Locules.*—Number (per fruit): Five (5). Length: About 10.5 mm. Width: About 4 mm. Form: Closed.

Seeds:

*Number per fruit.*—About 8 to 10.

*Number per locule.*—About 2.

*Shape.*—Ellipsoid, elongated and pointed.

*Length.*—About 8.20 mm.

*Width.*—About 4.75 mm.

*Color.*—Grey-brown, RHS 165A.

Use: Fresh market. Suitable as dessert apple from September to May in Italy.

Disease/pest resistance: For both tree and fruit of 'CIVNIRED S', similar to 'CIVNI', no unusual disease/pest resistance observed as of this time.

Disease/pest susceptibility: For both tree and fruit of 'CIVNIRED S', similar to 'CIVNI', no unusual disease/pest susceptibility observed as of this time. Susceptible to scab and slightly susceptible to powdery mildew.

Winter hardiness: Tolerant to temperatures down to −12° C. without observed damage to wood and buds of dormant apple trees.

Drought/heat tolerance: Tolerant to temperatures up to 40° C., growth is limited by drought periods without irrigation.

Shipping/storage characteristics: Keeps well in both common cold storage for about 5 months (until January in Italy) and in controlled atmosphere (ULO-conditions) for up to 8 months (until April in Italy).

What is claimed is:

1. A new and distinct *Malus domestica Borkh.* variety of apple tree named 'CIVNIRED S', as illustrated and described herein.

* * * * *

'CIVNIRED S'

'CIVNI'

'CIVNIRED S'

'CIVNI'

'CIVNIRED S' 'CIVNI'